United States Patent [19]

Cohen et al.

[11] Patent Number: 5,312,628
[45] Date of Patent: May 17, 1994

[54] ISOLATION OF A SOLUBLE 42 KD PANCREATIC ISLET CELL AUTOANTIGEN

[75] Inventors: Margo P. Cohen, New York, N.Y.; Van-Yu Wu, Cherry Hill, N.J.

[73] Assignee: Exocell, Inc., Philadelphia, Pa.

[21] Appl. No.: 59,719

[22] Filed: May 12, 1993

Related U.S. Application Data

[63] Continuation-in-part of Ser. No. 731,700, Jul. 18, 1991, abandoned, which is a continuation-in-part of Ser. No. 509,773, Apr. 17, 1990, abandoned.

[51] Int. Cl.$^5$ .................... C07K 15/06; A61K 39/00; G01N 33/564
[52] U.S. Cl. ........................ 424/88; 435/7.21; 530/350; 530/412; 530/416; 530/417; 436/506
[58] Field of Search .................. 424/88; 530/350, 412, 530/416, 417

[56] References Cited

U.S. PATENT DOCUMENTS

| | | | |
|---|---|---|---|
| 4,446,240 | 5/1984 | Nerenberg | 436/542 |
| 4,487,830 | 12/1984 | Coates et al. | 435/7 |
| 4,855,242 | 8/1989 | Soeldner | 436/539 |

OTHER PUBLICATIONS

Baekkeskov, S., et al. (1982) Nature 298: 167–69.
Karounos, D. G. et al. (1988) Diabetes 37, Supp. I: 30A (Abstract #120).
Roep, B. O., et al. (1991) Lancet 337: 1439–41.
McEvoy et al., "A Sensitive Assay to Detect Diabetes-Specific Islet Cell Surface Antibodies (ICSA) Prior to the Onset of Type I Diabetes (IDDM)," Diabetes (1989), vol. 38, suppl. 2, p. 86A, Abst. 343.
Dotta et al., "Immunoreactivity of Islet Tumor Cells: A New Diabetes–Associated Antigen," Clin. Res. (1988), Abstract, vol. 36, p. 480A.
Nayak et al., "Cystoplasmic" Islet Cell Antibodies Evidence that the Target Antigen is a Sialoglycoconjugate Diabetes (1985), 34:617–619.
Baekkeskov et al., "Antibodies to a 64,000 $M_r$ Humman Islet Cell Antigen Precede the Clinical Onset of Insulin–Dependent Diabetes," Clin. Invest. (1987), 79:926–934.
Baekkeskov, et al., Nature, 1990, vol. 347, pp. 151–156.

*Primary Examiner*—Robert J. Hill, Jr.
*Assistant Examiner*—David L. Fitzgerald
*Attorney, Agent, or Firm*—Banner, Birch, McKie & Beckett

[57] ABSTRACT

A method of isolating soluble pancreatic islet antigen employs extraction with a non-ionic detergent and fractionation on a gel filtration column. Fractions are screened for high immunoreactivity with diabetic serum which is positive for ICA immunofluorescence when tested on tissue sections of a pancreas from a human blood group O donor. The isolated soluble antigen is suitable for measuring autoantibodies in both complement fixation assays as well as ELISA-type and immunoblotting formats. Methods of using isolated soluble antigen to test serum for autoantibodies are also taught.

27 Claims, 2 Drawing Sheets

ISOLATION OF A SOLUBLE 42 KD PANCREATIC ISLET CELL AUTOANTIGEN

This application is a continuation-in-part of application Ser. No. 07/731,700, filed Jul. 18, 1991, which is a continuation-in-part of Ser. No. 07/509,773, filed Apr. 17, 1990, both abandoned.

THIS FIELD OF THE INVENTION

This invention relates to the field of auto-immune disease. In particular, it relates to the area of diabetes.

BACKGROUND OF THE INVENTION

Autoantibodies directed against the islet cells of the pancreas are indicators of ongoing beta cell destruction, predict preclinical disease, and identify susceptible individuals at risk for development of diabetes. Immunologic, genetic, and epidemiologic studies indicate that the majority of patients with insulin dependent diabetes mellitus (IDDM) have a long, clinically asymptomatic, prediabetic period. This phase is characterized by the presence of autoimmune phenomena and very subtle metabolic changes which antedate the clinical manifestations of insulin deficiency by many months or even years. Organ specific autoimmune reactions play an essential role in the development of progressive destruction of the insulin producing cells of the islets of Langerhans.

Type I diabetes is a chronic autoimmune disease with six major sequential stages (Eisenbarth, N. Engl. J. Med. 314: 136, 1986). Briefly, in genetically susceptible individuals (Stage I), an unidentified factor (Stage II) triggers the development of a variety of immunologic abnormalities (Stage III). These abnormalities precede a progressive loss of insulin secretion (Stage IV), until clinical diabetes becomes manifest (Stage V). At this point, some residual beta cell function persists, but almost complete destruction of the beta cells finally follows (Stage VI). Additionally, in patients with Type II (non-insulin dependent) and gestational diabetes, the presence of islet cell antibodies portends insulin deficiency and defines subgroups that have a slowly progressive form of Type I diabetes (Irvine et al., J. Clin Lab Immunol. 2: 23, 1979; Groop et al., Diabetes 35: 237, 1986; Steel et al., J. Lab. Clin. Immunol. 4: 83, 1980; DiMario et al., Diabetologia 25: 392, 1983; Tetsuro et al., Diabetes 36: 510, 1987; Gleichman et al., Diabetologia 27: 90, 1984). The rate of beta cell destruction is accelerated in patients with adult onset diabetes who have islet cell antibodies.

Islet Cell Antibodies (ICA) were originally detected by indirect immunofluorescence. Briefly, the patient serum is layered on an unfixed cryostat section of human pancreas from a blood group O donor. Binding of ICA to islet cells is then revealed with an antihuman IgG reagent, conjugated to fluorescein isothiocyanate, and detected with an ultraviolet microscope. If ICA are present in the serum, the cytoplasm of the Langerhans islet cells is stained, leaving the nuclei and the surrounding exocrine tissue unstained (Bottazzo et al., Lancet 2: 1279, 1974).

Various modifications have been introduced in attempts to improve the classic indirect immunofluorescent assay. These include use of: a) Bouin's fixed or paraffin embedded human pancreas instead of unfixed sections; b) monkey pancreas; c) acetone fixation of the tissue; d) prolonged incubation of the sera in the presence of aprotinin (a protease inhibitor); e) protein A labelled FITC as the second step reagent; f) microfluorometric apparatus to record fluorescence; g) immunohistochemical staining with glucose oxidase or peroxidase labelled protein A; h) counterstaining of the islets with monoclonal antibodies; and i) three step immunofluorescence with a biotin-avidin system (Ginsberg-Fellner and McEvoy, Autoimmunity and the Pathogenesis of Diabetes, Springer-Verlag, New York, 1990).

However, all of these assays have different degrees of specificity and sensitivity, and unknown intra- and inter-assay precision. These problems have been documented during International Workshops (1986, 1987) on the Standardization of Cytoplasmic ICA, which revealed poor inter-laboratory concordance for sera unless they were very high titer or were absolutely negative. These workshops also revealed a very broad range of end-point titers, which was ascribed to several factors but mainly related to variability in the expression of the antigenic determinants in the pancreatic tissue used in the different laboratories. The workshops have recommended preparation of an international standard ICA-positive reference serum and the establishment of common arbitrary units to express ICA results with the various methodologies employed by different laboratories. Nevertheless, it is clear that detection and quantification of islet cell antibodies by the various immunofluorescence and immunohistochemical assays is imperfect, imprecise, unstandardized, and dependent on unpredictable variables such as the freshness, source, availability, and preparation of human pancreas and the eye of the observer. As presently performed, these assays are suitable only for research projects.

The development of an immunoassay to detect and quantitate islet cell antibodies has been hampered by the lack of definition of the autoantigen(s) with which they react. A number of putative candidates have been described in the literature, including a 64 kD protein, a sialoglycolipid (ganglioside), a "polar" antigen, several other proteins of varying molecular weight, and a number of monoclonal antibody-defined antigens (Baekkeskov et al., J. Clin. Invest. 79: 926, 1987; Nayak et al., Diabetes 34: 617, 1985; Dotta et al., Clin. Res. 36: 480A, 1988; McEvoy et al., Diabetes 38: 86A, 1989). However, these substances have not been isolated in a soluble form suitable for routine clinical immunological assays. In addition, the methods used to detect the substances are not readily adaptable to a format that would be appropriate to the hospital or clinical laboratory. Thus there is a need in the art of diabetes treatment for isolated, soluble, islet cell antigens. There is also a need in the art for a method of accurately, objectively and simply determining the presence of autoantibodies that react with pancreatic islet cells.

SUMMARY OF THE INVENTION

Figure 1:
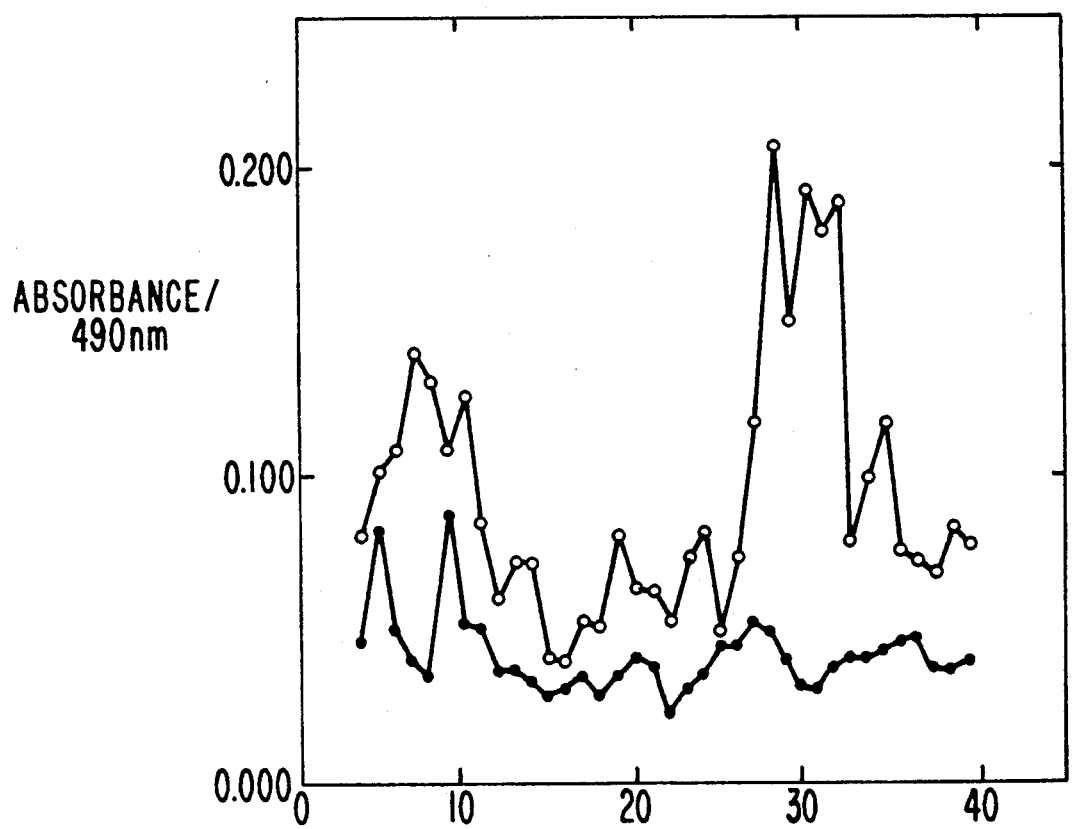
FIG. 1 shows a plot of ELISA absorbances of fractions of an islet antigen preparation eluted from an HPLC (DEAE-5pw) column. Closed circles represent reactivity with non-diabetic sera and open circles represent diabetic sera reactivity.

It is an object of the present invention to provide a cell-free antigenic preparation comprising soluble islet cell antigen that is reactive with circulating autoantibodies to pancreatic islet cells associated with diabetes mellitus.

It is another object of the present invention to provide a method for the isolation of antigens from the pancreas that are recognized by the autoantibodies reactive with islet cells which are associated with diabetes mellitus.

It is yet another object of the present invention to provide a method for detecting and quantitating circulating autoantibodies reactive with islet cells in biological specimens.

These and other objects of the invention are provided by one or more of the embodiments described below. In one embodiment a cell-free antigenic preparation is provided which comprises a soluble antigen reactive with circulating autoantibodies to pancreatic islet cells associated with diabetes mellitus, wherein said preparation immunologically binds at least two-fold less to serum from non-diabetic humans than to serum from diabetic humans, wherein said antigen has a molecular weight of about 42 kD when measured on SDS-polyacrylamide gels.

In another embodiment of the invention a method is provided for isolating antigens from the pancreas that are recognized by the autoantibodies reactive with islet cells which are associated with diabetes mellitus, said method comprising:

lysing and extracting islet cells from human pancreas to provide a cell-free extract containing soluble islet cell autoantigen;

fractionating components of the cell-free extract to provide fractionated component solutions;

testing the fractionated component solutions for reactivity with circulating autoantibodies to pancreatic islet cells associated with diabetes mellitus;

selecting the fractionated component solution with maximum reactivity.

In yet another embodiment of the invention an antigenic preparation is provided which is made by the method described above.

In still another embodiment of the invention a method for detecting and quantitating circulating autoantibodies reactive with islet cells is provide which comprises:

contacting a test sample of serum comprising antibodies with a cell-free antigenic preparation comprising soluble antigen reactive with circulating autoantibodies to pancreatic islet cells associated with diabetes mellitus; and detecting antigen-antibody complexes, the amount of antigen-antibody complexes providing a measure of autoantibodies in the test sample.

The present invention thus provides the art with the means to simply, accurately and reproducibly detect and measure the amount of circulating autoantibody to islet cells. This is useful in the screening, monitoring and therapy for diabetes.

DETAILED DESCRIPTION

It is a finding of the present invention that a sub-cellular component can be isolated in soluble form from pancreatic islet cells which is immunoreactive with ICA immunofluorescence positive sera. The component is immunoreactive with almost all ICA-positive sera tested, indicating that the component is a common autoantigen associated with diabetes.

According to the present invention, a cell-free extract containing soluble islet cell autoantigen is made by lysing and extracting islet cells from human pancreas. The HLA-type of the pancreas donors has not been found to affect the ability to isolate the islet cell autoantigen. We have isolated the islet cell autoantigen from pancreases isolated from donors having the following HLA types: HLA-DR 7; HLA-DR 1, w-11; HLA-DR 11,7; HLA-DR 2,4. We have found no pancreas from any HLA type which failed to yield the islet cell autoantigen of the present invention. Islet cells can be isolated from other pancreatic cells by collegenase digestion or other techniques known in the art. Alternatively, human pancreatic tissue can be used as a starting material without isolating islet cells, if fat and fibrous tissue are removed and the tissue minced and homogenized. Lysis of cells can be accomplished by any means known in the art. A preferred means involves repeated cycles of freezing and thawing the cells.

The lysate can be pelleted by centrifugation at about 30,000 to 110,000×g for about 1 hour; the pellet can be resuspended in buffer and again centrifuged. The pellet can be extracted with a non-ionic detergent, preferably Triton X-100 TM (polyethylene glycol tertoctylphenyl ether). Sodium dodecyl sulfate does not provide a suitable extract when used to extract the pellet, and its use should therefor be avoided. Preferably a protease inhibitor is also present to minimize degradation of proteins.

It is desirable that immunoglobulin molecules be removed from the preparation. This separation can be accomplished using a protein-A pak (Waters) on high pressure liquid chromatography (HPLC). Other means known in the art can also be used. Removal of immunoglobins from the preparation avoids non-specific immunoreactivity which can obfuscate the reaction of interest. Applicants have found that when the preparation is made from purified islet cells rather than pancreatic tissue that the preparation is devoid of significant amounts of immunoglobulins, even without performing a step to remove them.

The components of the extracted islet cells can be fractionated according to any means known in the art. Fractionation can be on the basis of size, change, affinity or other physicochemical property. In one preferred method, the extracted islet cells are fractionated by high pressure liquid chromatography (HPLC) on a Waters SW-300 gel filtration column or on a DEAE-5pw column. Fractions which elute from the column (or other fractionating means) are tested for immunoreactivity with an ICA immunofluorescence positive serum or combination of such sera. The antigen also can be tested for reactivity with sera from patients with new onset insulin dependent diabetes or with sera from relatives of diabetics in whom ICA by the immunofluorescent procedure is not detectable. The fractionated components with the maximum reactivity are selected. Preferably the fractionated components with maximum reactivity are at least two-fold less reactive with normal serum from ICA-negative persons with no family history of diabetes. The relative reactivity of normal sera and new onset insulin dependent diabetes sera varies, depending on the amount of ICA present in the latter sera. Preferably the antigenic components are purified substantially from other components which are not the subject of diabetes-specific, autoimmune phenomena.

The antigen of the present invention which is present in the islet cell preparations has been subjected to SDS-polyacrylamide gel electrophoresis and immunoblotted. This analysis determined the molecular weight of the protein (or a monomer thereof) to be between about 40 and 45 kDa. This molecular weight ranges is referred to herein as about 42 kDa. The native antigen may have a molecular weight which is larger than this if the protein identified is part of a larger oligomeric complex. The binding of the soluble antigen to ICA positive sera in immunoblots indicates that even when denatured the antigen is recognized by autoantibodies associated with diabetes mellitus.

The ICA immunofluorescence positive sera employed in the present invention contain circulating autoantibodies to pancreatic islet cells. These autoantibodies are associated with diabetes mellitus. The titer of the autoantibodies changes over the progression of the disease. Peak titers are often found to precede onset of disease symptoms. Often by the time of onset of diabetes, the autoantibodies are undetectable. Thus the measurement of autoantibodies can be used in many ways: to determine the prevalence of diabetes in populations; to monitor beta-cell destruction in pre-diabetics and in on-going diabetics; to monitor the effect of therapeutic protocols; to determine the need for insulin in gestational and adult-onset diabetes; and to predict impending insulin deficiency in individuals pre-disposed to diabetes.

The cell-free antigenic preparation comprising soluble antigen of the present invention can be used in assays for any of the purposes mentioned above. One assay format is a complement fixation assay. The complement fixation reaction (Weiser et al, *Fundamentals of Immunology*, Lea and Febiger, Philadelphia, 1970) is based on the principle that if an antigen-antibody reaction takes place in vitro in the presence of complement, the components of the complement system will participate and will be fixed or inactivated. Any remaining complement can then be detected by adding the indicator system, red blood cells (RBCs), plus antibody (hemolysin) specific for red blood cells. If complement is all consumed in the first reaction the red blood cells added will not undergo lysis. On the other hand, if specific antibody is not present in the test serum an antigen-antibody reaction will not take place in the first reaction and complement will not be fixed or consumed. This complement will be free to react with the red blood cells and hemolysin and will cause lysis of the red cells. Accordingly, if the red blood cells do not lyse when the indicator system is added, the reaction is "positive" (i.e. antibodies are present in the test serum). Conversely, if the red cells lyse in the indicator system, no complement-fixing antibody was present in the first reaction and the reaction is "negative".

According to one embodiment of the invention the complex of islet cell antigen and autoantibody is detected by incubation with complement, human erythrocytes and, for example, rabbit anti-human erythrocyte antibody. If no antigen-antibody complexes are present, the complement reacts with the erythrocytes and with the rabbit antibodies and causes hemolysis, which can be measured spectrophotometrically or observed by inspection. If antibody-antigen complexes are present they will bind the available complement and prevent hemolysis. Absence of hemolysis indicates the presence of serum antibody in the test sample which reacts with the antigen; the intensity of hemolysis is inversely related to the amount of antibody, providing a quantitative measure of the titer of antibody in the sample.

Alternatively, the soluble antigen of the present invention can be used in an ELISA type format. The antigen can be immobilized onto plastic microtiter plates, as is known in the art. Sera to be tested can be added to the plates and allowed to react with the antigen. Serum components which do not react with the immobilized antigen can be removed. An enzyme conjugated reagent can then be added to detect serum components (antibodies) bound to the antigen on the plates. Preferably the reagent is alkaline phosphatase-conjugated protein A, although other reagents, such as enzyme-conjugated anti-human immunoglobulin, can be used. The amount of enzyme activity (measured using a chromogenic substrate) is determined and is correlated with the amount of autoantibody present in the test sample. Other assay formats known in the art may be used to detect islet cell autoantibodies employing the antigenic preparation of the present invention.

ELISA and complement fixation assays may be used sequentially. That is to say that, for example, an ELISA test may be used to provide information about the presence and amount of antibody. Then a complement fixation assay could be performed on the same serum. The complement fixation assay provides information about the amount of complement-fixing autoantibodies present. This may provide the clinician with additional diagnostic information not available from an ELISA. Since not all autoantibodies are necessarily complement-fixing, and complement is involved in the destruction of beta-cells, the proportion of complement-fixing autoantibodies to ICA relative to all autoantibodies to ICA could indicate the stage or severity of disease.

The isolated antigen of the present invention can be used in an ELISA or complement fixation system, to detect the presence of islet autoantibodies even when reactivity is insufficient to yield positive immunofluorescence. The isolated antigen of the present invention is not reactive with sera from individuals who have no personal or family history of diabetes. This indicates that the antigen is diabetes specific, and contains a unique epitope against with which islet autoantibodies react.

The isolated antigen of the invention can be used by one of ordinary skill in the art to produce monoclonal antibodies after immunization of animals with pancreatic or islet cell extract purified as described herein. The animal will recognize and respond to the epitopic determinants of the immunizing antigen by producing antibodies to these epitopic determinants. By immortalizing the B-cells produced by the immunized animal, according to techniques well known in the art, hybridomas can be isolated which secrete antibodies which are specific for the antigen of the invention. Alternatively, an unpurified pancreatic or islet cell extract can be used to immunize animals and the purified antigen of the invention can be used to screen for antibodies having specificity for the antigen of the invention.

Thus it is possible to identify antibodies with the same epitopic specificity as the circulating autoantibodies associated with diabetes mellitus. These antibodies can be used to greatly simplify and reduce the amount of purification needed to make the antigenic preparations of the invention. In addition, such antibodies can also be used in other assay formats. For example, the antibodies specifically reactive with the antigen of the invention can be used in immunofluorescence assays to compete with ICA for binding to tissue sections. Competition of the antibodies specific for the antigen of the invention with the patient autoantibodies indicates that a specific interaction is occurring between patient serum and tissue section which is relevant to diabetes. Further, the antibodies specific for the antigen of the invention can be used to quantitate the amount of autoantibodies by measuring the amount of specific antibody required to compete with the serum antibody. This could enable standardization of the immunofluorescence assays even while continuing to employ variable tissue sections as substrates.

The antigen of the invention can also be prepared by recombinant DNA techniques or chemical synthesis. The amino acid sequence of any protein portion of the antigen of the invention can be determined by standard techniques, provided the purified antigen of the invention. The cDNA encoding that amino acid sequence can be isolated and molecularly cloned using the amino acid sequence information. For example, a set of probes can be synthesized which include all possible codons for some of the amino acids of the antigen. These probes can be used to screen cDNA libraries of pancreatic cell DNA. Alternatively, antibodies reactive with the antigen of the present invention can be used to screen expression libraries of human pancreatic DNA to identify the expressed gene. The gene can be expressed in non-human systems to produce the antigen in quantity. Other alternative strategies can be used, as are known in the art, for molecular cloning of a purified protein.

The antigen of the invention can be bound to many different carriers and used to detect the presence of circulating autoantibodies as well as experimentally generated antibodies reactive with the antigen of the invention. Examples of well known carriers include glass, polystyrene, polyvinyl chloride, polypropylene, polyethylene, polycarbonate, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antigen or antibody, or will be able to ascertain such, using routine experimentation.

As discussed above, the soluble antigen of the invention can be used in assay formats which do not require labeling, e.g., ELISA tests and immunoblots. However, the antigen can be labeled also. There are many different labels and methods of labeling known to those of ordinary skill in the art which can be used to detect antigen-antibody interaction and/or complement fixation. Examples of the types of labels which can be used in the present invention include enzymes, radioisotopes, colloidal metals, fluorescent compounds, chemiluminescent compounds, and bioluminescent compounds. Those of ordinary skill in the art will know of other suitable labels for binding to the antigen or to the antibody which recognizes the unique epitopic determinant, or will be able to ascertain such, using routine experimentation. Furthermore, the binding of these labels to the antigen of the invention can be done using standard techniques known to those of ordinary skill in the art.

As used in this invention, the term islet cell antigen is meant to include any material containing an epitopic determinant capable of specific interaction with circulating islet autoantibodies, and capable of inhibiting the specific interaction of the antigen of the invention with those antibodies. The islet cell antigen need not actually be made in or isolated from islet cells. As discussed above, the antigen or parts of the antigen containing epitopic determinants can be chemically synthesized or made in other organisms using recombinant DNA techniques.

The amount of antigen used in assays according to the present invention is diagnostically effective. That is, it is sufficient in quantity to enable detection and quantitation of the circulating islet autoantibodies having the idiotype with which the epitopic determinants of the antigen of the invention specifically react, i.e., those associated with diabetes mellitus.

The antigen preparations of the present invention, whether purified from human pancreas or obtained from another source or method, have many uses other than in assays. They can be used therapeutically to treat patients in the pre-diabetic, early onset, or diabetic phases of the disease. For example, the preparations can be administered to humans to desensitize them to the antigen, i.e., to inhibit their bodies from making more autoantibodies specifically reactive with the antigen. Alternatively, the antigen preparations can be administered to humans to compete with the beta cells for autoantibody binding and thereby reduce beta cell destruction. Similarly, the antigenic preparations can be administered to inhibit T cells specific for the antigens. Such T cells are known to be involved in the destruction of beta cells.

Anti-idiotypic antibodies specific for the paratope of the autoantibodies which are specific for the antigen of the invention can also be raised. These can be raised using the monoclonal antibodies taught above. Anti-idiotypic antibody generation and isolation are well known in the art. Such antibodies can be used therapeutically to compete with circulating autoantibodies to decrease beta cell destruction.

The above disclosure generally describes the present invention. A more complete understanding can be obtained by reference to the following specific examples which are provided herein for purposes of illustration only, and are not intended to limit the scope of the invention.

EXAMPLE 1

Preparation Of Islet Antigens From Pancreas And From Purified Islets

Authentic islet antigen was prepared from either autopsy specimens of human pancreas or from islets that had been isolated, after collagenase digestion, from pancreatic tissue. The pancreases were isolated from donors having the following HLA types: HLA-DR 7; HLA-DR 1, w-11; HLA-DR 11,7; HLA-DR 2,4. The pancreas was freed of fat and fibrous tissue before further preparation. The tissue was minced in solution (1:5; wt:vol) containing 0.15M NaCl, 0.05M Tris, pH 7.4, and aprotinin (10 ug/ml), and was homogenized in a precooled blender for two minutes at maximum speed. Isolated islets were frozen in 1 ml of Tris/saline and thawed in a warm water bath three times to lyse the cells. After centrifugation at $31,000 \times g$ for 1 hour at 4° C., the supernatant was removed. The pellet was again mixed with Tris/saline, centrifuged, and the supernatant removed. The pellet was then extracted twice with 1% Triton X-100 ™ (polyethylene glycol tertoctylphenyl ether) in Tris/saline buffer containing 10 ug/ml aprotinin, each time followed by centrifugation, and the supernatants were combined and filtered through a Protein-A pak on HPLC to remove IgG molecules. The Triton extract was then fractionated on HPLC with a Waters SW-300 gel filtration column in Tris/saline buffer containing 0.05% Triton. Eluates were collected at a flow rate of 0.5 ml/min, collecting eluates sequentially into individual tubes of one minute per tube.

EXAMPLE 2

Identification Of Islet Antigen Reactive With Islet Antibodies In Diabetic Serum Aliquots of each serially collected HPLC fraction of the Triton extracts of pancreatic islets prepared as described in Example 1 were immobilized onto plastic microtiter wells for 18 hours at 4° C. with glycine coupling buffer, pH 8.5. Ten μl of each fraction were coupled to an individual well, with the order of the wells corresponding to the order of the fractions collected sequentially from HPLC. After washing with Tris/saline containing 0.05% Tween 20 TM (polyoxyethylene sorbitan monolaurate) to remove unbound material, blocking for 2 hours at room temperature with 4% bovine serum albumin in coupling buffer, and washing with 0.05% Tween 20 TM (polyoxyethylene sorbitan monolaurate) in saline, test serum from non-diabetic (ICA immunofluorescence negative) or diabetic (ICA immunofluorescence positive) subjects was added and allowed to react for two hours at room temperature. The sera had been reacted with Protein A-sepharose to concentrate immunoglobulins of the IgG class which contains the autoantibodies specific for the antigen of the invention and had been diluted (1:500) in saline containing 0.1% BSA and 0.05% Tween 20 TM (polyoxyethylene sorbitan monolaurate), pH 7.4. After washing with saline/0.05% Tween 20 TM (polyoxyethylene sorbitan monolaurate), alkaline phosphatase (AP)-conjugated Protein A (1:250 dilution in PBS/0.01% BSA) was added and incubated for one hour at room temperature. Following extensive washes with saline/Tris, color was developed with an AP substrate and amplification system, (Bethesda Research Laboratories, Gaithersburg, Md.) and the absorbance recorded in an ELISA reader.

TABLE 1

| HPLC Tube No. | Absorbance Non Diabetic | Diabetic |
| --- | --- | --- |
| 1 | .02 | .06 |
| 2 | .06 | .07 |
| 3 | .02 | .08 |
| 4 | .02 | .08 |
| 5 | .07 | .07 |
| 6 | .02 | .08 |
| 7 | .01 | .07 |
| 8 | .04 | .138 |
| 9 | .03 | .507 |
| 10 | .03 | .526 |
| 11 | .05 | .553 |
| 12 | .18 | 1.036 |
| 13 | .22 | 1.233 |
| 14 | .17 | .955 |
| 15 | .07 | .301 |
| 16 | .03 | .346 |
| 17 | .01 | .08 |
| 18 | .01 | .09 |
| 19 | .006 | .04 |
| 20 | .01 | .06 |
| 21 | .00 | .10 |
| 22 | .00 | .08 |
| 23 | .00 | .13 |
| 24 | .06 | .15 |
| 25 | .02 | .13 |
| 26 | .02 | .19 |

TABLE 1-continued

| HPLC Tube No. | Absorbance Non Diabetic | Diabetic |
| --- | --- | --- |
| 27 | .02 | .14 |
| 28 | .02 | .17 |
| 29 | .02 | .16 |
| 30 | .02 | .16 |
| 31 | .02 | .07 |
| 32 | .08 | .07 |

As seen in Table 2, there is clear reactivity of diabetic serum with HPLC fractions 12-16 of the Triton extract, with little or no reactivity of the non-diabetic serum with the same fractions. Fraction 13 had the maximum activity and is referred to here as "HPLC 13." It was used in the complement fixation assay described below.

EXAMPLE 3

Alternative Preparation of Pancreatic Islet Cell Antigen

Freshly frozen human pancreas, was obtained within several hours of death, thawed in Tris/saline buffer, pH 7.4 containing 10 ug/ml aprotinin, minced and gently digested with collagenase (Sigma Chemical Co.) to liberate islets from acinar tissue. The digest was centrifuged at 20,000 rpm for 30 minutes at 4° C., washed twice with Tris/saline/aprotinin buffer and centrifuged. The pellet was passed through a nylon mesh sieve of 220 um pore size, and the filtrate was collected by centrifugation for one hour at 20,000 rpm. The aqueous supernatant was removed, and the buffy coat was again mixed with Tris/saline, centrifuged, and re-collected as described above. The preparation then was extracted twice with 1% Triton X-100 TM (polyethylene glycol tertoctylphenyl ether) in Tris-saline buffer containing 10 ug/ml aprotinin, each time followed by centrifugation at 20,000 rpm for one hour, and the supernatants combined. The triton extract was used for SDS gel-electrophoresis and immunoblotting, and also was further fractionated on HPLC.

The triton extract was fractionated on a Waters HPLC with a DEAE-5pw (ion exchange) column pre-equilibrated with 20 mM Tris, pH 8.5 containing 0.05% Triton X-100 TM (polyethylene glycol tertactylphenyl ether) and eluted with a linear salt gradient (0–0.3M NaCl) in the same buffer. Eluates were collected at a flow rate of 1.2 ml/min., collecting eluate into separate tubes of one minute per tube. The eluate fractions were sequentially collected and used in an ELISA system to determine reactivity with serum samples. 10 ul aliquots of each fraction were individually coupled to sequential wells and reacted with non-diabetic sera (closed circles) and diabetic sera (open circle). See FIG. 1.

Pooled, concentrated material eluting in fractions 26-33 revealed a discrete band at Mol wt. approx. 42,000 upon immunoblotting with ICA positive serum, and no band at this molecular weight upon immunoblotting with non-diabetic sera.

EXAMPLE 4

Detection of Islet Antibody in Diabetic Serum Using Islet Antigen HPLC 13 and a Complement Fixation Assay Ten μl of each test sample (serum) was incubated for 30 minutes at 56° C. with 40 μl Tris saline buffer containing 0.01M Ca$^{++}$ to inactivate endogenous complement. Three tests were run: (a) diabetic serum which was ICA immunofluorescence positive; (b) the same serum in the absence of HPLC13; and (c) non-diabetic serum from a patient with no family history of diabetes which was ICA immunofluorescence negative. After incubation, 25 μl were removed and added to test tubes containing 10 μl of HPLC13 islet antigen, following which 10 μl of normal serum containing complement was added and the mixture was incubated at room temperature for 30 minutes. This mixture was called reagent A. Ten μl of Type O human erythrocytes, 10 μl of rabbit antihuman erythrocyte antibody (5 mg in 2 ml of Tris saline containing 0.01M $Ca^{++}$) and 180 μl of saline/Tris/$Ca^{++}$ were then added to 25 μl of reagent A, and the mixture incubated at 37° C. for 10 to 30 minutes. (The erythrocytes are prepared by collecting 1 ml of whole blood into a citrated tube, centrifuging and washing the erythrocytes twice with Tris/saline buffer, and reconstituting the erythrocytes into 1 ml of saline/Tris/$Ca^{++}$ buffer.) An aliquot was removed for microscopic examination, the mixture was centrifuged and the supernatant collected. Hemolysis was determined visually and spectrophotometrically at an absorbance of 415 nm.

TABLE 2

| Test Serum | Antigen | RBC Agglutination | Hemolysis Visual (pinkness) | Absorbance at 415 nm |
| --- | --- | --- | --- | --- |
| (a) Diabetic | HPLC13 | ± | — | .140 |
| (b) Normal | HPLC13 | +++ | +++ | .500 |
| (c) Diabetic | none | ++++ | ++++ | .580 |

As shown in Table 2, the specific complexes of islet antigen in HPLC13 and islet cell autoantibodies present in diabetic test serum binds available complement to prevent red blood cell (RBC) agglutination and hemolysis. In contrast, non-specific antibodies present in normal serum do not recognize islet antigen in HPLC13, and complement-mediated hemolysis occurs. Complement-mediated hemolysis also occurs with diabetic serum if no HPLC13 is present to react with the islet antibodies and fix complement.

EXAMPLE 5

Detection of Islet Antibody in Diabetic Serum Using Islet Antigen and Immunoblots Islet antigen preparations were subjected to SDS polyacrylamide gel electrophoresis in parallel with molecular weight standards. The gels were blotted to transfer the proteins to nitrocellulose. The nitrocellulose blots were incubated with ICA-positive diabetic sera or with ICA-negative nondiabetic sera.

Figure 2:
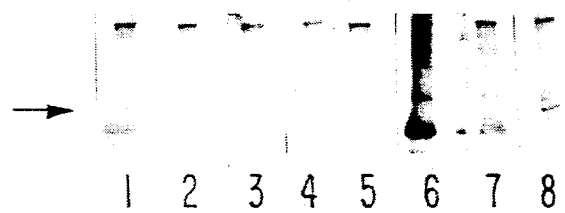
FIG. 2 shows a stained immunoblot with control and diabetic sera and islet antigen preparations. Lanes 1–3 and 7–8 are diabetic sera and lanes 4–6 are nondiabetic sera.

As shown in FIG. 2, sera from diabetic patients detected a protein of about 42 kD (lanes 1–3 and 7–8) in the islet antigen preparations which was not detected by the control sera. Ten ICA-positive diabetic sera and ten ICA-negative nondiabetic control sera were tested by this method. All of the diabetic sera detected the approximately 42 kD protein while none of the control sera detected it.

We claim:

1. A cell-free antigenic preparation useful for measuring autoantibody titers in blood, said preparation comprising a detergent-soluble antigen which immunologically binds to circulating autoantibodies to pancreatic islet cells associated with diabetes mellitus, wherein said preparation immunologically binds at least two-fold less to antibodies in serum from non-diabetic humans than to antibodies in serum from diabetic humans, wherein said antigen has a molecular weight of between 40 and 45 kD when measured on SDS-polyacrylamide gels, wherein said antigen is obtainable from pancreases of humans having an HLA type selected from the group consisting of HLA-DR 7; HLA-DR 1, w-11; HLA-DR 11,7; and HLA-DR 2,4, and wherein said antigen is substantially purified from other antigens which are not immunologically reactive with diabetes-specific, islet cell antibodies.

2. The preparation of claim 1 wherein said antigen immunologically binds to said circulating autoantibodies in the denatured state.

3. The preparation of claim 1 wherein the soluble islet cell antigen is not radiolabeled.

4. The preparation of claim 1 wherein the soluble islet cell antigen is not reduced.

5. The preparation of claim 1 which is devoid of sodium dodecylsulfate.

6. A cell-free antigenic preparation useful for measuring autoantibody titers in blood, said preparation comprising a detergent-soluble antigen which immunologically binds to circulating autoantibodies to pancreatic islet cells associated with diabetes mellitus, wherein said preparation immunologically binds at least two-fold less to antibodies in serum from non-diabetic humans than to antibodies in serum from diabetic humans, said antigen being substantially purified from other antigens which are not immunologically reactive with diabetes-specific, islet cell antibodies, said antigen having a molecular weight of between 40 and 45 Kd when measured on SDS-polyacrylamide gels, said antigen being obtainable from pancreases of humans having an HLA type selected from the group consisting of HLA-DR 7; HLA-DR 1, w-11; HLA-DR 11,7; and HLA-DR 2,4, said antigenic preparation made by the process of:
lysing and extracting islet cells from human pancreas to provide a cell-free extract containing soluble islet cell autoantigen;
fractionating components of the cell-free extract to provide fractionated soluble components;
testing the fractionated soluble components in denatured state for immunological binding to circulating autoantibodies to pancreatic islet cells associated with diabetes mellitus;
selecting the fractionated soluble components with maximum immunological binding in the denatured state.

7. The preparation of claim 6 wherein:
immunoglobulin molecules are removed from the lysed and extracted cells.

8. The preparation of claim 7 wherein immunoglobulin molecules are removed from the lysed and extracted islet cells using a protein-A column on HPLC.

9. The preparation of claim 6 wherein:
the step of fractionating is on the basis of size.

10. The preparation of claim 9 wherein:
the step of fractionating is on a Waters SW-300 gel filtration column on HPLC.

11. The preparation of claim 6 wherein:
the step of fractionating employs an ion exchange resin.

12. The preparation of claim 11 wherein:
the ion exchange resin is DEAE-5pw.

13. The preparation of claim 6 wherein:
the step of fractionating employs SDS-polyacrylamide gel electrophoresis.

14. The preparation of claim 6 wherein the step of lysing is done by freezing and thawing the islet cells.

15. The preparation of claim 6 wherein the step of extracting employs Triton X-100 ™ (polyoxyethylene glycol tert-octlyphenyl ether).

16. The preparation of claim 6 wherein islet cells are isolated from pancreatic tissue after collagenase digestion.

17. A method for isolating a detergent soluble autoantigen which is capable of immunologically binding to circulating autoantibodies to pancreatic islet cells associated with diabetes mellitus, wherein said autoantigen immunologically binds at least two-fold less to antibodies in serum from non-diabetic humans than to antibodies in serum from diabetic humans, said autoantigen being substantially purified from other antigens which are not immunologically reactive with diabetes-specific islet cell antibodies, said autoantigen having a molecular weight of between 40 and 45 kD when measured on SDS-polyacrylamide gels, said antigen being obtainable from pancreases of humans having an HLA type selected from the group consisting of HLA-DR 7; HLA-DR 1, w-11; HLA-DR 11,7; and HLA-DR 2,4, said method comprising:

lysing and extracting islet cells from human pancreas to provide a cell-free extract containing said soluble islet cell autoantigen;

fractionating components of the cell-free extract to provide fractionated soluble components;

testing the fractionated soluble components in the denatured state for immunological binding to circulating autoantibodies to pancreatic islet cells associated with diabetes mellitus;

selecting the fractionated soluble components with maximum immunological binding in the denatured state.

18. The method of claim 17 wherein:
immunoglobulin molecules are removed from the lysed and extracted islet cells.

19. The method of claim 18 wherein immunoglobulin molecules are removed from the lysed and extracted islet cells using a protein-A column on HPLC.

20. The method of claim 17 wherein:
the fractionation is on the basis of size.

21. The method of claim 20 wherein:
fractionation is on a Waters SW-300 gel filtration column on HPLC.

22. The method of claim 17 wherein:
the fractionation employs an ion exchange resin.

23. The preparation of claim 22 wherein:
the ion exchange resin is DEAE-5pw.

24. The method of claim 17 wherein:
the fractionation employs SDS-polyacrylamide gel electrophoresis.

25. The method of claim 17 wherein the step of lysing is done by freezing and thawing the islet cells.

26. The method of claim 17 wherein the step of extracting employs Triton X-100 ™ (polyoxyethylene glycol tert-octylphenyl ether).

27. The method of claim 17 wherein islet cells are isolated from pancreatic tissue after collagenase digestion.

* * * * *